(12) United States Patent
Steinbauer et al.

(10) Patent No.: US 6,346,623 B1
(45) Date of Patent: Feb. 12, 2002

(54) METHOD FOR PRODUCING SUBSTITUTED PYRIDINE-CARBOXYLIC ACIDS

(75) Inventors: Gerhard Steinbauer, Enns; Curt Zimmermann, Mauthausen; Ernst Wressnegger; Erich Steinwender, both of Linz, all of (AT)

(73) Assignee: DSM Fine Chemicals Austria Nfg GmbH & CoKG, Linz (AT)

( * ) Notice: Subject to any disclaimer, the term of this patent is extended or adjusted under 35 U.S.C. 154(b) by 0 days.

(21) Appl. No.: 09/701,543
(22) PCT Filed: Jun. 4, 1999
(86) PCT No.: PCT/EP99/03882
§ 371 Date: Nov. 30, 2000
§ 102(e) Date: Nov. 30, 2000
(87) PCT Pub. No.: WO99/67217
PCT Pub. Date: Dec. 29, 1999

(30) Foreign Application Priority Data

Jun. 22, 1998 (AT) .............................................. 1069/98

(51) Int. Cl.[7] ............................................. C07D 213/55
(52) U.S. Cl. ...................................................... 546/320
(58) Field of Search ........................................ 546/320

(56) References Cited

PUBLICATIONS

O'Murchu, C., Synthesis, pp. 880–882, 1989.

*Primary Examiner*—Jane Fan
(74) *Attorney, Agent, or Firm*—Wenderoth, Lind & Ponack, LLP

(57) ABSTRACT

An improved process for the preparation of substituted pyridinecarboxylic acids (II), useful as herbicide intermediates, by ozonolysis of quinolines (I).

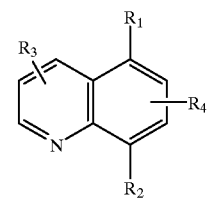

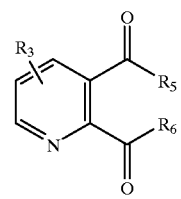

7 Claims, No Drawings

METHOD FOR PRODUCING SUBSTITUTED PYRIDINE-CARBOXYLIC ACIDS

This application is a 371 of PCT/EP99/03882 Jun. 4, 1999, now W099/67217.

Substituted pyridinecarboxylic acids are important raw materials for the synthesis of herbicides, making the preparation on an industrial scale of great importance. One method for the preparation of substituted pyridinecarboxylic acids is the ozonolysis of the corresponding substituted quinolines (O'Murchu, Synthesis (1989) pp. 880–882), where the quinoline starting material, which has a basic function, is dissolved in a mixture of water and acetic acid by the addition of sulfuric acid as sulfate, and the ozonolysis is carried out in this solution. Depending on the substitution of the pyridinecarboxylic acid, the reaction mixture is further oxidized with hydrogen peroxide, particularly if substituted pyridine-2,3-di-carboxylic acids are desired as reaction products.

An industrially significant product is 2-acetylnicotinic acid, which can be prepared by ozonolysis of 8-methylquinoline. However, if a corresponding synthesis is carried out on an industrial scale, byproducts arise, which are virtually impossible to remove from the product by crystallization as a result of which the high purity required for the further reaction cannot be achieved. As the structure of such byproducts which are difficult to remove, substituted pyridinecarboxylic acids alkylated on the pyridine ring have been found. In the case of the ozonolysis of 8-methylquinoline for the preparation of 2-acetylnicotinic acid, 2-acetyl-4-methylnicotinic acid and 2-acetyl-6-methylnicotinic acid are found, the 4-methyl derivative remaining in the product in the case of one crystallization from a solvent such as ethyl acetate, methyl tert-butyl ether, acetone, tetrahydrofuran, toluene, methyl isobutyl ketone, butanol or water.

The cause of this byproduct formation was found in a content of a few ppm of iron in the reaction mixture. In an industrial plant which is at least partially constructed from constituents whose material is stainless steel, traces of iron are virtually unavoidable, particularly if, as in the present case, the process is carried out in aqueous strongly acidic solution.

The object of the present invention was therefore to find an improved industrial process for the preparation of substituted pyridinecarboxylic acids by ozonolysis of a correspondingly substituted quinoline in which the described byproduct formation can be prevented, even in the presence of traces of metals such as iron.

Accordingly, the invention provides an improved process for the preparation of substituted pyridinecarboxylic acids by ozonolysis of quinolines, which is characterized in that a quinoline of the formula

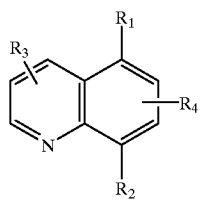

I which is substituted in position 2 and/or 3 and/or 4 by $R_3$, and in position 6 and/or 7 by $R_4$, where $R_1$ and $R_2$ are H or a $C_1$–$C_3$-alkyl group and $R_3$ and $R_4$ are a group which is inert under the reaction conditions, and at least one of the radicals $R_1$ and $R_2$ is not H, is reacted with ozone in aqueous acidic solution at temperatures of from –5 to +40° C., the resulting solution is maintained at a temperature of from 0 to 100° C. for 0.5 to 15 hours with the introduction of oxygen or air for decomposition of the peroxides formed, and the corresponding substituted pyridinecarboxylic acid of the formula

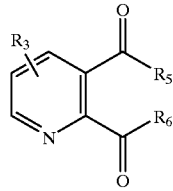

II in which $R_3$ is as defined above, and $R_5$ and $R_6$ are OH or $C_1$ to $C_3$-alkyl, where at least one of the radicals $R_5$ and $R_6$ is not OH, is isolated from the reaction mixture.

In the process according to the invention, quinolines of the formula I are converted to substituted pyridinecarboxylic acids of the formula II. Suitable quinolines are substituted here in position 5 or 8 by a methyl, ethyl, isopropyl or n-propyl group. Also, the quinolines may be substituted in position 2 and/or 3 and/or 4 by hydrogen, $C_1$–$C_3$-alkyl or alkoxy groups, halogen etc. Preferably, only one of positions 2, 3 or 4 is substituted, and the quinolines used as starting material particularly preferably have hydrogen as substituent in position 2, 3 and 4. The quinolines suitable as starting materials can also be substituted in position 6 and/or 7 by a group which is inert under the reaction conditions, such as, for example, by a $C_1$–$C_3$-alkyl or alkoxy group, halogen, etc. Preference is also given to those quinolines which are substituted in position 8 by a methyl or ethyl group and where position 5 is occupied by hydrogen. Examples thereof are 8-methylquinoline and 3-ethyl-8-methylquinoline. Particular preference is given to using 8-methyl-quinoline.

The starting materials are either available commercially or can be prepared, for example, by the Skraup synthesis, as described, for example in C. O'Murchu, Synthesis 1989, pp. 880–882.

The corresponding reaction is carried out according to the invention in aqueous acidic solution. Examples of acids which are suitable here are mineral acids, such as sulfuric acid, nitric acid or phosphoric acid.

Where appropriate, an additional solvent, such as, for example, acetic acid, methanol, etc. may also be added. However, the use of acetic acid is preferably avoided so that the ozonolysis is exclusively carried out in aqueous mineral acid as solvent for the substituted quinoline. Particular preference is given to using an aqueous sulfuric acid solution. The amount of mineral acid is of little significance. If, apart from the aqueous mineral acid, no further solvent (such as e.g. acetic acid) is used, then a sufficient amount of mineral acid must of course be used to form a salt of the quinoline, i.e. in the case of sulfuric acid 0.5 equivalents or in the case of nitric acid 1 equivalent, based on the substituted quinoline, in order to achieve a homogeneous solution of the starting mixture.

The starting material is dissolved in the aqueous acidic solution, the aim being for the concentration of starting material to be between 2 and 30% by weight, preferably between 2.5 and 10% by weight. Lower concentrations of starting material increase the yield of the desired end product. An ozone-bearing stream of $O_2$ is passed into the resulting solution until the equivalent amount of ozone or an excess has been absorbed. The end and thus the reaction time is determined by the consumption of the theoretical amount of ozone and can also be readily ascertained from an increased appearance of ozone which occurs simultaneously. The end of the reaction can also be readily ascertained using a suitable in process check on the extent of reaction of the substituted quinoline.

The temperature of the ozonolysis is −5 to +40° C. Preferably, a temperature of from 0 to +10° C. is chosen. After the ozonolysis, the peroxides which form as intermediates are decomposed by heating the solution, forming the desired substituted pyridinecarboxylic acid. The temperature during the peroxide decomposition can be between 0 and 100° C., preferably at about 50 to 70° C. The time for the peroxide decomposition naturally depends on the temperature chosen and lasts, for example at 60° C. for about 2.5 hours. For the process according to the invention, no further oxidizing agent, such as hydrogen peroxide, is required for the peroxide decomposition.

Oxygen is simultaneously introduced into the reaction solution during the peroxide decomposition period. Oxygen can be used here in the form of pure oxygen or in the form of air. This measure prevents the formation of end products alkylated in position 4 or 6. The peroxide decomposition is carried out until a peroxide residual content of at most 5 mmol/l is achieved. A residue of peroxides can also be destroyed by the addition of a reducing agent, such as, for example, sodium pyrosulfite, prior to further work-up. If only very small ppm amounts of iron are present in the reaction mixture, then the formation of the pyridinecarboxylic acids substituted by alkyl groups in the 4- or 6-position can be minimized by terminating the peroxide decomposition and reducing peroxide residue which are present using reducing agents since the free-radical secondary reaction preferably takes place at the end of the peroxide decomposition.

In this case, the introduction of oxygen can optionally be dispensed with. The byproduct content should not exceed 0.1 percent by weight (determined e.g. by means of HPLC or GC).

The desired end product is isolated from the reaction solution by means of extraction. The pH during the extraction should be below 4, preferably below 2.5. The desired pH is preferably set using sodium hydroxide or potassium hydroxide.

Suitable solvents for the extraction are, preferably, toluene, methyl tert-butyl ether, ethyl acetate or n-butanol.

Particular preference is given to using ethyl acetate or methyl tert-butyl ether as extractant. After the extraction, the organic phase is concentrated by evaporation, preferably to a concentration of from 10 to 30% by weight of product, and, at −10 to +10° C., the desired end product crystallizes out.

During the evaporation of the organic solvent, in cases where this solvent forms an azeotrope with water, then water is also removed azeotropically.

Using the process according to the invention, the desired substituted pyridinecarboxylic acids of the formula II are obtained in yields of 70–80%. The purity of the products is >98%. The process according to the invention is preferably used for the preparation of 2-acetylnicotinic acid (ANA).

ANA is obtained here in yields of 70–75% and a purity of >98%. Undesired byproducts such as 2-acetyl-4-methylnicotinic acid do not form or form only in negligible amounts.

The pyridinecarboxylic acids prepared according to the invention are, as a result of their purity, particularly suitable as a starting material for the preparation of herbicides, and 2-acetylnicotinic acid is preferably suitable for the preparation of herbicides based on substituted semicarbazones.

The invention accordingly also provides for the use of the pyridinecarboxylic acids prepared according to the invention for the preparation of herbicides.

EXAMPLE 1 (COMPARATIVE EXPERIMENT)

12 kg of 8-methylquinoline (84 mol) were dissolved in 250 liters of water and 9.5 kg of 60% strength nitric acid (90 mol). The solution was cooled to 1° C., and a stream of oxygen which contained 60 g/m$^3$ of ozone was introduced into this solution. This was continued until the residual content of 8-methyl-quinoline in the solution was about 1 g/l (determination by means of GC). The solution was then heated at 60° C. for 4 hours for decomposition of the peroxides. The endpoint of the peroxide decomposition was determined by means of titration (potassium iodide, sodium thiosulfate, starch) . The residual peroxide content was 1 mmol/l. Three batches carried out identically were purified. A content of 12 ppm of iron was found in the peroxide solution.

The pH was adjusted to 1 using 50% strength sodium hydroxide solution, and the solution was extracted counter-currently with ethyl acetate in the phase ratio 1/1 using a sieve-plate extractor. The extract was concentrated to a volume of about 180 liters by distilling off ethyl acetate. The solution was cooled to −5° C., and the product was filtered off using a pressure filter, washed with prechilled ethyl acetate and dried on the pressure filter in vacuo.

This gave 28 kg (67% of theory) of 2-acetylnicotinic acid which, according to GC and HPLC, contained 0. 75% of 2-acetyl-4-methylnicotinic acid.

In this way, batches containing up to 9.1% of 2-acetyl-4-methylnicotinic acid were obtained.

EXAMPLE 2

A stream of oxygen was introduced into 300 ml of an ozonized solution prepared analogously to Example 1. 40 mg of iron(II) sulfate heptahydrate, corresponding to a content of 25 ppm of iron, were added to the solution, and the mixture was heated at 60° C. for 2.5 hours with the further introduction of oxygen. A peroxide content of 3 mmol/l was found by titration. Adjustment of the pH to pH 1 with 50% strength sodium hydroxide solution and extraction with ethyl acetate gave 2-acetylnicotinic acid in which no 2-acetyl-4-methylnicotinic acid byproduct was detectable.

EXAMPLE 3

250 kg of 8-methylquinoline (1.75 kmol) were dissolved in 3200 liters of water and 180 kg of 96% strength sulfuric acid (1.75 kmol) . The solution was cooled to a temperature of 1° C., and then a stream of oxygen which contained 50 to 60 g/M$^3$ of ozone was introduced. This was continued until the residual content of 8-methylquinoline was about 1 gram/liter (determination by means of GC). After the ozonolysis, the reaction mixture was let down into a reactor which contained 2000 liters of water at a temperature of 60° C. 2 m$^3$ of air per hour were continuously introduced into the aqueous solution during the peroxide decomposition. The peroxide decomposition was carried out for 2 hours at a temperature of 60° C. until the peroxide residue content was 3 to 5 mmol/liter (titration). 50% strength sodium hydroxide solution was used to establish a pH of from 1.5 to 2, and the solution was extracted countercurrently with methyl tert-butyl ether in the methyl tert-butyl ether/aqueous solution phase ratio=1.5/1 using a sieve-plate extractor. The extract was concentrated to a concentration of about 10% by weight by distilling off methyl tert-butyl ether. The solution was cooled to −10° C., and the product was filtered over a pressure filter, washed with prechilled methyl tert-butyl ether and dried on the filter in vacuo.

This gave 202 kg (70% of theory) of 2-acetyl-nicotinic acid. According to HPLC, the purity was 98.5%; no 2-acetyl-4-methylnicotinic acid was detectable as byproduct.

What is claimed is:

1. An improved process for the preparation of substituted pyridinecarboxylic acids by ozonolysis of quinolines, wherein a quinoline of the formula

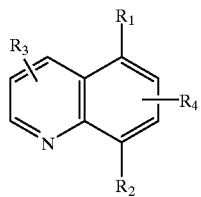

I which is substituted in position 2 and/or 3 and/or 4 by $R_3$, and in position 6 and/or 7 by $R_4$, where $R_1$ and $R_2$ are H or a $C_1$–$C_3$-alkyl group and $R_3$ and $R_4$ are a group which is inert under the reaction conditions, and at least one of the radicals $R_1$ and $R_2$ is not H, is reacted with ozone in aqueous acidic solution at temperatures of from −5 to +40° C., the resulting solution is maintained at a temperature of from 0 to 100° C. for 0.5 to 15 hours with the introduction of oxygen or air for decomposition of the peroxides formed, and the corresponding substituted pyridinecarboxylic acid of the formula

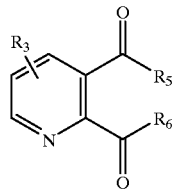

II in which $R_3$ is as defined above, and $R_5$ and $R_6$ are OH or $C_1$ to $C_3$-alkyl, where at least one of the radicals $R_5$ and $R_6$ is not OH, is isolated from the reaction mixture.

2. The process as claimed in claim 1 wherein the quinoline of the formula I used is 8-methylquinoline or 3-ethyl-8-methylquinoline.

3. The process as claimed in claim 1 wherein the aqueous acidic solution used is an aqueous sulfuric acid, nitric acid or phosphoric acid solution.

4. The process as claimed in claim 1 wherein the reaction with ozone is carried out at 0 to +10° C.

5. The process as claimed in claim 1 wherein the peroxide decomposition is carried out at 50–70° C.

6. The process as claimed in claim 1 wherein oxygen is introduced in the form of pure oxygen or in the form of air.

7. The process as claimed in claim 1 wherein the substituted pyridinecarboxylic acid is isolated from the reaction mixture by means of extraction.

* * * * *